United States Patent [19]

Kogure

[11] Patent Number: 4,886,366
[45] Date of Patent: Dec. 12, 1989

[54] REFERENCE CORRECTED COLOR SENSOR

[75] Inventor: Yasuo Kogure, Tokyo, Japan

[73] Assignee: Hoya Corporation, Tokyo, Japan

[21] Appl. No.: 131,489

[22] Filed: Dec. 10, 1987

[30] Foreign Application Priority Data

Dec. 10, 1986 [JP] Japan ................... 61-292454

[51] Int. Cl.$^4$ .................. G01N 21/27; G01J 3/46
[52] U.S. Cl. ................... 356/406; 356/319; 356/425; 356/448
[58] Field of Search ............... 356/448, 328, 405, 406, 356/425, 319; 250/227

[56] References Cited

U.S. PATENT DOCUMENTS

| 3,562,539 | 2/1971 | Beroza et al. ............ 250/227 |
| 4,152,075 | 5/1979 | Rellstab et al. ............ 250/227 X |
| 4,278,353 | 7/1981 | Ostermayer, Jr. ............ 356/448 X |
| 4,568,186 | 2/1986 | Yoshimura et al. ............ 356/328 X |

FOREIGN PATENT DOCUMENTS

| 2714043 | 3/1977 | Fed. Rep. of Germany . |
| 2606675 | 9/1977 | Fed. Rep. of Germany . |
| 3244286 | 11/1982 | Fed. Rep. of Germany . |
| 227510 | 9/1985 | Fed. Rep. of Germany ...... 356/319 |
| 2386813 | 11/1978 | France . |

OTHER PUBLICATIONS

Jacobowitz et al., "Determining Reflectometer Head Correction Factors" IBM Tech Disc. Bulletin, vol. 19 #6, pp. 2174-2175, Nov. 1976. copy 356/448.

Primary Examiner—Vincent P. McGraw
Attorney, Agent, or Firm—Sughrue, Mion, Zinn, Macpeak & Seas

[57] ABSTRACT

A color sensor comprising a plurality of detecting units. One of the detecting units may inspect the color of an object to be examined, and the other may inspect the color of the reference object simultaneously and independently. The reflected light of the object to be examined is corrected by the reflected light of the reference object. The lights reflected from the object to be examined and the reference object are derived from the same light source.

3 Claims, 2 Drawing Sheets

REFERENCE CORRECTED COLOR SENSOR

BACKGROUND OF THE INVENTION

1. Industrial Field of the Invention

The present invention relates to a color sensor for use in inspecting and controlling colors of such products as color prints, products coated with color paint, plastic products, foods, chemicals and so on including raw materials for the above of them being conveyed on the production line.

2. Prior Art

In FIG. 4, there is shown a known arrangement including a color sensor, which comprises a light source 1 for emitting illuminating light, light guides 2, a probe 3, a light receiving device 4, an amplifier 5 and an object 6 being examined, and an arrow 7 indicating extraneous disturbing light.

The color sensor thus constituted is disadvantageous in that, when the intensity/color of the illuminating light changes or when extraneous light is incident on the object being examined, the output value of the light receiving device 4 differs from the measured one that ought to be indicated.

In order to remedy this drawback, the extraneous light should be shut out while a light source for emitting illuminating light free from a change in intensity/color is used. However, it is almost impossible to provide such a light source for emitting illuminating light completely free from variations in intensity/color.

A color sensor shown in FIG. 5 has been proposed to solve the aforesaid problem. As shown in FIG. 5, this color sensor comprises light receiving devices 4a, 4b, a comparing operational device 8 and other parts with reference characters given to corresponding or like parts of FIG. 4. In the case of the color sensor thus constituted, the output value can be corrected, even though its illuminating light changes, by correcting the output value of one light receiving device 4b receiving the light reflected from an object 6 being examined while making use of the output value of the other light receiving device 4a for directly receiving the illuminating light from the light source.

Notwithstanding, the color sensor of FIG. 5 is still vulnerable to extraneous light as in the case of what is shown in FIG. 4 however sophisticatedly it may be contrived. In other words, the color of the object will have to be examined while the extranous light is shut out by, for istance, taking out the object being examined from the conveyor belt and putting it into a darkbox or arranging the conveyor belt in a darkroom.

However, any one of the aforesaid techniques will make the production line inconvenient for use, thus decreasing productivity.

Another known arrangement is to create the same condition as that in the darkroom by having a probe directly contact an object being examined. In this case, it incurs the risk of bruising the object being examined.

SUMMARY OF THE INVENTION

In view of the aforesaid problems, an object of the present invention is to provide a color sensor having a plurality of detecting means each for simultaneously independently inspecting the color of an object being examined.

According to the present invention, illuminating light fluctuation or extraneous disturbing light is prevented from affecting color inspection.

DETAILED DESCRIPTION

Figure 1:
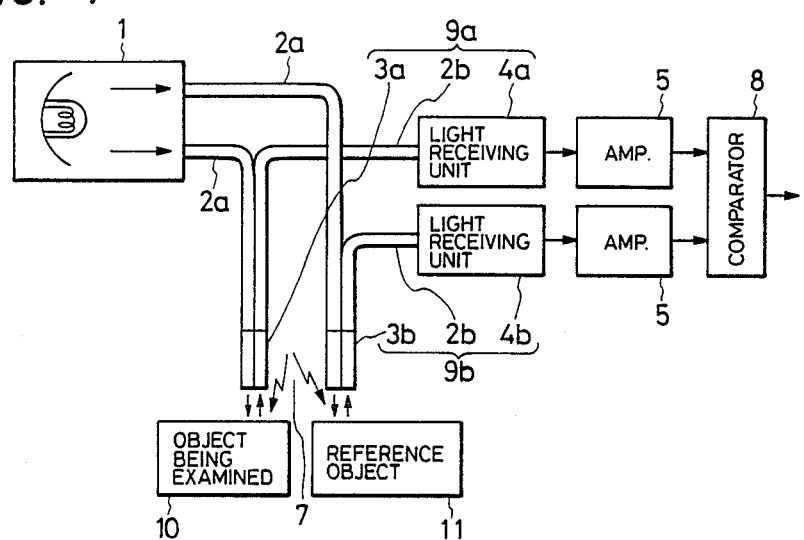
FIG. 1 is a system diagram of a color sensor embodying the present invention.
Figure 5:
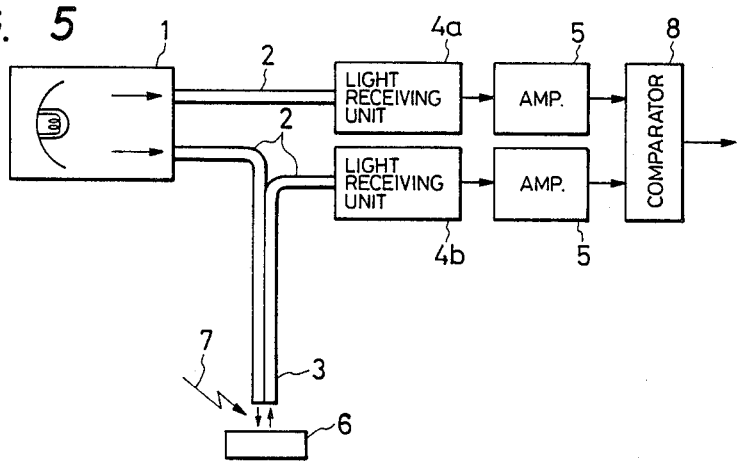

FIG. 1 is a system diagram of a color sensor embodying the present invention, wherein there is shown an arrangement including illuminating fibers 2a; detecting fibers 2b; an object detecting unit 9a consisting of the detecting fiber 2b, a probe 3a and a light receiving device 4a; a reference detecting unit 9b consisting of the detecting fiber 2b, a probe 3b and a light receiving device 4b; an object 10 being examined; and a reference object 11. In FIG. 1, like reference characters are given to corresponding or like parts of FIG. 5.

The color sensor according to the present invention has at least a pair of detecting units and the minimum essential number of detecting units is illustrated in FIG. 1.

Given that the intensities of light reflected from the object 10 being examined and the reference object 11 are y and y2 when the object 10 being examined and the reference object 11 are simultaneously respectively illuminated via the illuminating fibers 2a, y and y2 will not change even though they are examined any number of times, provided that illuminating light is completely kept constant and that disturbing light, i.e., the light introduced from the outside, is not present. In other words, stable color inspection is possible. Under the actual circumstances of inspection, the intensity and color tone of the light from the light source often vary with time and color inspection may not be practcally effected in a darkroom or darkbox (in such a case that the color inspection is carried out on the belt line, etc.). Accordingly, the present invention is intended to make possible stable light inspection under unfavorable circumstances.

The operation of the color sensor according to the present invention will subsequently be described. In reference to the color sensor of FIG. 1, one of the two detecting units is used to examine a standard white board or standard sample, whereas the other is used to examine the object being examined. Both the detecting units 9a, 9b are simultaneously triggered to effect the color inspection at the same time. Although the object 10 being examined and the reference object 11 are illuminated by the light disturbed because of the illuminating light fluctuation and the disturbing light, the light reflected from both the objects 10, 11 is always subject to changes at the same rate since the detecting units 9a, 9b are designed to allow only the reflected light of the illuminating and disturbing lights to be incident thereon because of the effective angular aperture thereof. More specifically, given that the changing rate is K and that y and y2 after being changed are respectively y' and y2', $$y' = y \times k$$
$$y2' = y2 \times k$$

From the equations above, $$y = y'/(y2'/y2) \qquad (1)$$

From Eq. (1) the value y can be computed from the values y', y2', provided y2 is measured beforehand. That is, the fluctuation affecting the reference object 11 is used to correct the measured value of the object 10 being examined to obtain a value when no fluctuation is present, i.e., the measured value in such a condition that no disturbing light exists under stable illumination.

The operation of each of the detecting units 9a, 9b when the reflected light is converted into three different kinds of light in color will subsequently be described. In this case, it is assumed that each of the light receiving devices 4a and 4b functions as a device which what is capable of three color separation and measurement of the quantity of light of each color thus obtained. With the value obtained by amplifying the output of one of the detecting units as a reference value, the comparing operational circuit 8 shown in FIG. 1 is used to compare the reference value with an amplified output value of another unit.

A description will first be given of a case where a standard white board is employed as the reference object 11. The color sensor according to the present invention is capable of the specifications of colorimetric system defined by L*, a*, b* and etc., as well as three color detection, because three-color separation by means of each detecting device follows a color matching function matching human eye luminous efficiency. The measured values of three colors are expressed by X, Y, Z, where variables are defined with accompanying letters as follows:

X, Y, Z: colors of the object being examined after their fluctuations are corrected (three prestimulus values);

L*, a*, b*: colors of the object being examined after their fluctuations are corrected (color specifications of L*, a*, b*);

$X_1$, $Y_1$, $Z_1$: three prestimulus values of the object detecting unit 9a for examining the object when it is affected by the change of illumination and the incidence of the disturbing light;

$X_2$, $Y_2$, $Z_1$: three prestimulus values of the reference detecting unit 9b for examining the standard white board when it is affected by the change of illumination and the incidence of the disturbing light;

$Xn_2$, $Yn_2$, $Zn_2$: three prestimulus values of the reference detecting unit 9b as values with those obtained by initially examining the standard white board as standards in the state where the illumination is constant without the extraneous light.

Given the degree of variability, on the basis of the above definition the fllowing equations are therefore also valid:

$$X_1 = X \times K, \; Y_1 = Y \times K, \; Z_1 = Z \times K$$
$$X_2 = Xn_2 \times K, \; Y_2 = Yn_2 \times K, \; Z_2 = Zn_2 \times K$$

therefore, $$X = X_1/(X_2/Xn_2) \qquad (2)$$
$$Y = Y_1/(Y_2/Yn_2) \ldots$$
$$Z = Z_1/(Z_2/Zn_2)$$

Chromaticity is obtainable therefrom as follows:

$$x = X/(X+Y+Z), \; y = Y/(X+Y+Z) \qquad (3)$$

Given three prestimulus values measured by the object unit 9a examining the standard white board in the state where the illumination is constant without the extraneous light are $Xn_1$, $Yn_1$, $Zn_1$, the values of L*, a*, b* in the colorimetric system can be expressed as follows:

$$L^* = 116(Y/Yn_1)^{1/3} - 16 \qquad (4)$$
$$a^* = 500\{(X/Xn_1)^{1/3} - (Y/Yn_1)^{1/3}\}$$
$$b^* = 200\{(Y/Yn_1)^{1/3} - (Z/Zn_1)^{1/3}\}$$

Figure 2:
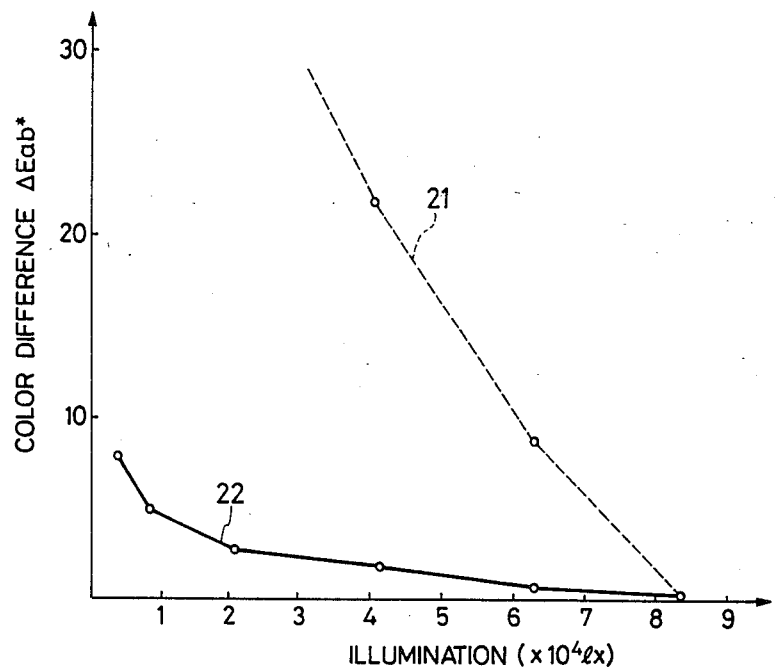
FIGS. 2 and 3 are graphs illustrating color differences based on the values measured by the color sensor of FIG. 1.
Figure 3:
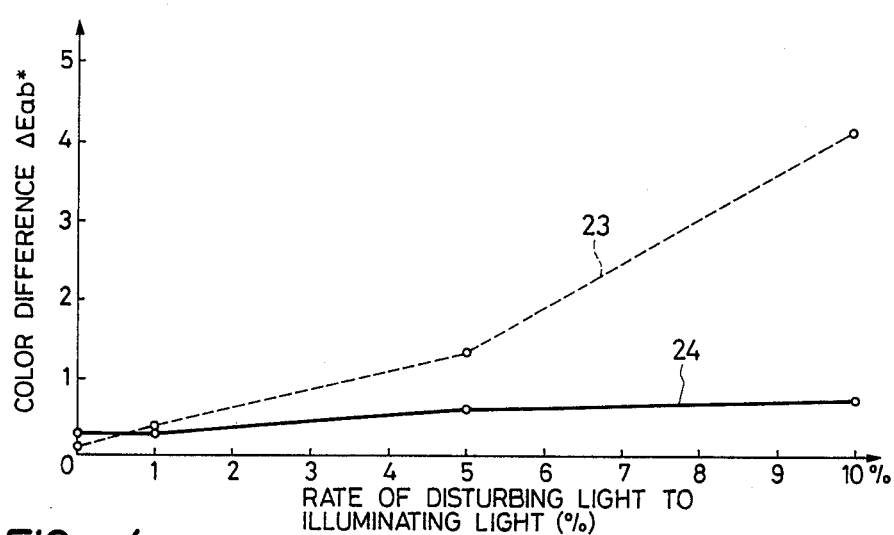
Figure 4:
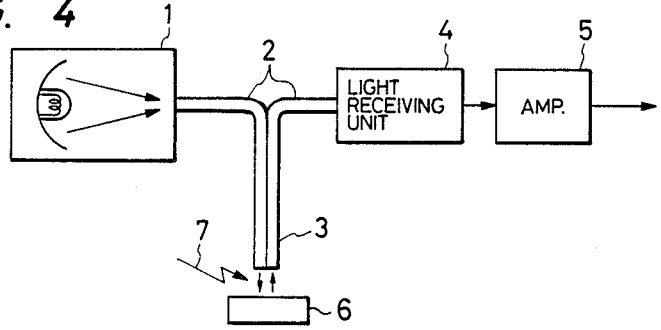
FIGS. 4 and 5 are system diagrams of conventional color sensors.

FIG. 2 shows the color difference ΔEab* computed according to the three prestimulus values obtained by changing the illumination of the light and correcting the illumination according to Eq. (2), on the other hand, FIG. 3 shows the color difference ΔEab* computed according to the three prestimulus values obtained by changing the ratio of the disturbing light to the illuminating light and correcting the disturbing light according to Eq. (2). FIGS. 2 and 3 are graphs showing the actual measured values when a white board, together with the detecting units 9a, 9b, is used as an object being examined. In other words, the three prestimulus values measured by both the detecting units 9a, 9b are ideally the same and the color difference ΔEab* becomes zero. In FIGS. 2, 3, the dotted lines 21, 23 designate a case where no correction has been made, whereas continuous lines 22, 24 designate that the correction has been made. As shown in these figures, the color difference ΔEab* between the detection units 9a, 9b with the correction made is by far smaller than what is present without the correction and brought close to an ideal state.

As set forth above, there are provided the plurality of detecting units, each being capable of examining the color simultanesoulsy and independently, and therefore the illuminating light fluctuation and the disturbing light are prevented from affecting the measured values. This makes possible the effective inspection of the light reflected from the object being examined under fluctuating illumination, with accuracy without covering the object in normal operating condition. Since the non-contact inspection of the color of any product is possible, it consequently incurs no risk of bruising the product. Moreover, the accurate inspection made possible without interrupting the flow of products on the production line contributes to increasing production line efficiency and reducing inspection cost to a greater extent.

I claim:

1. A color sensor, comprising:
a first detecting unit and a second detecting unit, each of said detecting units separating respective received beams into three color components and measuring respective quantities of light of said color components;
a reference object;

an object being examined;

means for illuminating said reference object and said object being examined with light;

first means for directing a portion of said light reflected from said reference object to said first detecting unit;

second means for directing a portion of light reflected from said object being examined to said second detecting unit; and means for comparing corresponding pairs of said measured quantities of light of said color component produced by said first and second detecting units, thereby correcting a measured color of said object being examined.

2. A color sensor as recited in claim 1, wherein said illuminating means comprises a single light source for illuminating both said reference object and said object being examined.

3. A color sensor as recited in claim 2, wherein said illuminating means comprises two optical fibers extending from said single light source to said reference object and said object being examined respectively, said first directing means comprises an optical fiber extending from said reference object to said first detecting unit, and said second directing means comprises an optical fiber extending from said object being examined to said second detecting unit.

* * * * *